United States Patent [19]
Marhold et al.

[11] 4,179,461
[45] Dec. 18, 1979

[54] PROCESS FOR THE PREPARATION OF DIPHENYL ETHERS

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 929,464

[22] Filed: Jul. 31, 1978

Related U.S. Application Data

[63] Continuation of Ser. No. 731,474, Oct. 12, 1976, abandoned.

[30] Foreign Application Priority Data

Oct. 21, 1975 [DE] Fed. Rep. of Germany ...... 2547037

[51] Int. Cl.$^2$ ............................................. C07C 41/00
[52] U.S. Cl. ............................. 260/465 H; 568/585; 568/586; 260/465 E; 260/465 F; 260/465 G; 260/607 AR; 260/609 F; 260/570.5 P; 260/568; 260/570.5 S
[58] Field of Search ........... 260/612 R, 465 H, 465 E, 260/465 F, 465 G, 607 AR, 609 F, 568, 570.5 P, 570.5 S; 568/585, 586

[56] References Cited

U.S. PATENT DOCUMENTS

| 3,824,295 | 7/1974 | Gordon | 260/614 R |
| 3,840,605 | 10/1974 | Gordon | 260/614 R |
| 3,992,432 | 11/1976 | Napier et al. | 260/465.1 |

FOREIGN PATENT DOCUMENTS

2037781 2/1972 Fed. Rep. of Germany .

OTHER PUBLICATIONS

McKillop et al., Tetrahedron, vol. 30, (1974), 1379–1382.
Herriott et al., Tetrahedron Letters, No. 44, (1972), 4521–4524.

*Primary Examiner*—Bernard Helfin
*Attorney, Agent, or Firm*—Sprung, Felfe, Horn, Lynch & Kramer

[57] ABSTRACT

In a process for the preparation of a diphenyl ether substituted in the 4,4'-position and/or the 2,2'-position relative to the ether oxygen atom by reaction of a reactive benzene compound substituted in the 1-position and the 2- or 4-position with a salt of nitrous acid, the improvement in that the reaction is carried out in the presence of a quaternary onium salt in water.

3 Claims, No Drawings

PROCESS FOR THE PREPARATION OF DIPHENYL ETHERS

This is a continuation of application Ser. No. 731,474, filed Oct. 12, 1976 and now abandoned.

The invention relates to a new process for the preparation of diphenyl ethers, substituted in the 4,4'-position and/or the 2,2'-position, by reaction of reactive benzene compounds, which are substituted in the 1-position and the 4-position or in the 1-position and the 2-position, with salts of nitrous acid.

A process for the preparation of 4,4'-disubstituted diphenyl ethers by reaction of reactive p-substituted halogenobenzene or nitrobenzene compounds with sodium nitrite is known from DT-OS (German Published Specification) No. 2,037,781. The reaction is carried out in polar organic solvents ($\epsilon<7$) at temperatures of 100° to 220° C. The molar ratio of the reactive 1,4-disubstituted benzene compound:sodium nitrite is 1:1 to 4.5.

However, the process has the serious disadvantage that small amounts of nitrophenolates which, in the organic solvents used, tend towards explosive decomposition at temperatures above 100° C., are formed as by-products. The process is therefore too unsafe for use on an industrial scale (see Houben-Weyl, 4th edition, 1963, volume VI/2, page 35).

A further process for the preparation of 4,4'-disubstituted diphenyl ethers is described in DT-AS (German Published Specification) No. 1,290,147. According to this process, 1-halogeno-4-nitro-phenyl compounds are condensed, in polar organic solvents in the presence of a concentrated aqueous alkali metal hydroxide, to form 4,4'-dinitro-diphenyl ethers. This reaction has the disadvantage that it can be used only for the preparation of those diphenyl ethers which do not contain any groups sensitive to alkali, for example which do not contain a nitrile, carboxylic acid amide, ester or trifluoromethyl group.

SUMMARY OF THE INVENTION

Broadly, this invention contemplates an improvement in a process for the preparation of a diphenyl ether substituted in the 4,4'-position and/or the 2,2'-position relative to the ether oxygen atom, wherein a reactive benzene compound substituted in the 1-position and the 4- or 2-position is contacted with a salt of nitrous acid by carrying out the process in the presence of a quaternary onium salt in water.

It has now been found, surprisingly, that it is possible, by reacting reactive benzene compounds with nitrites, to prepare diphenyl ethers, substituted in the 4,4'-position and/or the 2,2'-position, in a simple manner and without danger and without undesired by-products being formed when the reaction is carried out in non-polar organic solvents but in the presence of quaternary onium compounds in water. This result is surprising because it was to be expected according to the state of the art that, under the reaction conditions employed, namely heating in aqueous solutions rendered alkaline with sodium carbonate, the reactive benzene compounds would be saponified to phenols. The process according to the invention also has the advantage that the costly working up of the organic solvents is dispensed with. With the procedure according to the invention, the substituted diphenyl ethers are in most cases obtained direct in a crystalline form and can be separated off from the aqueous reaction solution in a simple manner. Furthermore, with the aid of the process according to the invention it is also possible to prepare substituted diphenyl ethers which are substituted by groups sensitive to alkali.

The diphenyl ethers substituted in the 4,4'-position and/or the 2,2'-position, which can be prepared according to the invention, are preferably diphenyl ethers of the formula

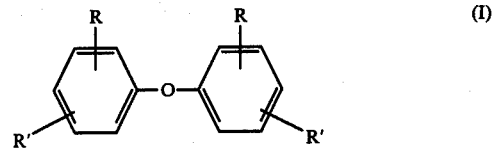

in which
  R denotes a $NO_2$, CN or $R''SO_2$ group which is in the ortho-position or para-position relative to the ether oxygen atom and
  R' denotes hydrogen, fluorine, chlorine, a $C_1$–$C_4$-alkyl, $C_1$–$C_4$-alkoxy or $C_1$–$C_4$-alkylmercapto radical, which is optionally substituted by halogen, or the $N(R'')_2$ radical,
in which
  R'' repesents alkyl or aryl which is optionally substituted by halogen.

The reactive benzene compounds substituted in the 1-position and 4-position or the 1-position and 2-position, which are to be used as starting compounds, correspond, in particular, to the formula

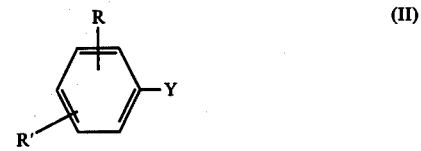

in which
  Y denotes a halogen atom or the nitro group,
  R denotes a $NO_2$, CN or $R''SO_2$ group which is in the ortho-position or para-position relative to Y and
  R' has the meaning indicated under formula I.

Examples of R' and R'' which may be mentioned are: as $C_1$–$C_4$-alkyl radicals which are optionally substituted by halogen, above all the methyl and trifluoromethyl radical, as $C_1$–$C_4$-alkoxy radicals which are optionally substituted by halogen, above all the methoxy and trifluoromethoxy radical and, as $C_1$–$C_4$-alkylmercapto radicals which are optionally substituted by halogen, the methylmercapto and trifluoromethylmercapto radical.

For R'', possible aryl radicals are, above all, optionally substituted phenyl radicals, for example phenyl radicals substituted by $C_1$–$C_4$-alkyl or halogen, such as the phenyl, chlorophenyl, 2,4-dichlorophenyl, tolyl and xylyl radical.

The quaternary onium salts to be used according to the invention are quaternary ammonium and phosphonium salts of the formula

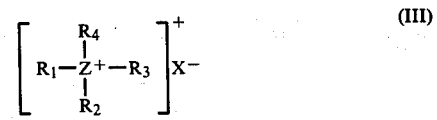

in which
- Z represents nitrogen or, preferably, phosphorus,
- $R_1$, $R_2$, $R_3$ and $R_4$ independently of one another denote optionally substituted alkyl, cycloalkyl, aralkyl or aryl, or two adjacent radicals amongst $R_1$, $R_2$, $R_3$ and $R_4$, together with the central atom Z and optionally further hetero-atoms, form a heterocyclic structure and
- $X^{3\ominus}$ represents a halide, cyanide or hydroxyl ion.

Examples of $R_1$, $R_2$, $R_3$ and $R_4$ which may be mentioned are: as alkyl radicals, above all $C_1$–$C_{18}$-alkyl radicals, such as the methyl, ethyl, propyl, butyl, heptyl, hexyl, dodecyl and octadecyl radical; as aralkyl radicals, benzyl radicals which are optionally substituted by $C_1$–$C_4$-alkyl radicals or methoxy groups or halogen; as aryl radicals, above all phenyl radicals which are substituted by $C_1$–$C_4$-alkyl or $C_1$–$C_2$-alkoxy groups or by halogen atoms and, as cycloalkyl radicals, cyclopentyl and especially cyclohexyl radicals, which are optionally substituted by $C_1$–$C_4$-alkyl radicals.

Examples which may be mentioned of heterocyclic structures which can be formed by two adjacent radicals amongst $R_1$, $R_2$, $R_3$ and $R_4$, together with the central atom Z and optionally further hetero-atoms, such as oxygen, sulphur or nitrogen, are, above all, 5-membered and 6-membered heterocyclic structures, such as the pyrrolidine, piperidine or morpholine ring.

The following may be mentioned as examples of representatives of the onium salts to be used according to the invention: tetraethyl-ammonium chloride, tetrabutyl-ammonium bromide, tetrabutyl-ammonium iodide, triethyl-benzyl-ammonium chloride, methylbutyl-piperidinium iodide, tetraethyl-ammonium bromide, tetrabutyl-ammonium chloride, benzyl-methyl-piperidinium iodide, tetraethyl-ammonium cyanide, benzyltrimethyl-ammonium hydroxide, benzyltrimethyl-ammonium cyanide, triphenylbenzyl-phosphonium bromide, benzyldodecyldimethyl-ammonium chloride, cyclohexyloctyldimethyl-ammonium chloride and tetrabutyl-phosphonium chloride.

Quaternary onium salts of the formula III in which $R_1$ and $R_2$ independently of one another represent $C_1$–$C_4$-alkyl and $R_3$ represents $C_1$–$C_4$-alkyl or benzyl and $R_4$ represents $C_1$–$C_{14}$-alkyl or phenyl, or $R_1$ and $R_2$ together with the nitrogen atom form a 5-membered or 6-membered heterocyclic structure, have proved particularly useful.

The amount of quaternary onium salt can vary within wide limits. In general, 0.1 to 10% by weight, preferably 2 to 5% by weight, based on the weight of the reactive benzene compound to be reacted, have proved useful.

In general, the process according to the invention is carried out by heating the reactants, that is to say the reactive benzene compounds of the formula II, alkali metal nitrites or alkaline earth metal nitrites, quaternary onium compounds and water, to temperatures of 100°–220° C., preferably 100°–150° C., if appropriate, whilst stirring, until the reaction has ended.

In order to reach temperatures above 100° C., it is appropriate to carry out the reaction in closed reaction vessels under pressure. Reaction temperatures of up to 130° C. can also be achieved without the use of pressure by using supersaturated salt solutions. In most cases, the diphenyl ether formed is obtained in a crystalline form and can be filtered off direct. If necessary, the crude product can be purified by known methods, for example by recrystallisation.

In order to bind the nitrous gases formed during the reaction, alkali metal carbonates or alkaline earth metal carbonates are advantageously also added to the reactants.

In order to prepare the reaction mixture, alkali metal nitrites or alkaline earth metal nitrites, alkali metal carbonates or alkaline earth metal carbonates and quaternary onium compounds are dissolved in water and the benzene compound to be reacted is added to the solution. The sequence in which the reactants are mixed with one another is not important. In order to achieve reasonable reaction times it is essential that the benzene compound is at least partially in the liquid phase. This condition is met when the benzene compound dissolves, at least to a limited extent, for example to the extent of 1%, in the aqueous salt solution at the reaction temperatures and/or when the melting point of the benzene compound is below the reaction temperature, that is to say the benzene compound is in the molten state.

The amount of water is not critical and can be varied within wide limits. It is possible to choose a small amount of water and to carry out the reaction with solutions, of the inorganic salts, which are saturated when hot; it is also possible to use dilute aqueous solutions, for example 10% strength solutions, of the inorganic salts. It has proved to be most advantageous so to choose the amount of water that both the inorganic salts which are employed and the salts which are formed during the reaction are dissolved at room temperature.

The benzene compound and the nitrite are generally employed in a ratio of 1 mol of benzene compound:1-.5–2.5 equivalents of nitrite. When this ratio is used, the amount of carbonate is advantageously about 1 mol of carbonate per mol of phenyl compound.

The quaternary onium compounds used as catalysts can be recovered and re-used. For recovery, the crystalline organic reaction product is washed with an organic solvent, for example alcohol, and this solution is concentrated. The residue essentially consists of the quaternary onium compound and still contains only small amounts of the reaction product and/or the starting material. The remaining fraction of the quaternary onium compound can be recovered by extracting the aqueous salt solution. The onium compound obtained in this way, which has been freed from solvents and still contains small amounts of organic material, can be re-used to catalyse the reaction.

The 4,4′-dinitro-diphenyl-ether can be reduced in known manner with hydrogen and raney-nickel as catalyst to the corresponding diamines. The diamines are starting materials for polyamides which can be obtained for example in a polymerisation-reaction with pyro mellitic acid dianhydrid (DAS No. 12 02 981 and U.S.S.R. Pat. No. 293 070).

EXAMPLE 1

A reaction mixture consisting of 35 g (0.51 mol) of sodium nitrite, 20 g (0.19 mol) of sodium carbonate, 80 ml of water, 2 g (0.012 mol) of tetraethyl-ammonium chloride and 45 g (0.2 mol) of 4-chloro-3-nitro-benzotrifluoride is heated to the reflux temperature for 2 hours. After cooling, the precipitate is filtered off and washed with a little dilute hydrochloric acid and then with a little water. The product, which has been pressed off well, is recrystallised from alcohol. Yield: 30 g (76% of theory) of 2,2′-dinitro-4,4′-di-(trifluoromethyl)-diphenyl ether. (Melting point: 106°–107° C.).

EXAMPLE 2

A mixture consisting of 86 g (1.25 mols) of sodium nitrite, 53 g (0.5 mol) of sodium carbonate, 300 ml of water, 6 g (0.02 mol) of tetrabutyl-phosphonium chloride and 78.5 g (0.5 mol) of 4-chloro-nitrobenzene is heated, in an autoclave, to 140° C. for 5 hours, whilst stirring and under the autogenous pressure. After cooling and letting-down the autoclave, the solid product is filtered off from the aqueous solution and washed, first with 50 ml of water and then with 100 ml of methanol.

The methanol solution is collected separately and concentrated to dryness since, in addition to a little reaction product, it contains the catalyst and the latter can be re-used.

The crystalline reaction product is dried. 60 g (90% of theory) of 4,4'-dinitro-diphenyl ether (melting point: 140°-141° C.) are obtained.

EXAMPLE 3

A mixture consisting of 40 g (0.255 mol) of 2-chloronitrobenzene, 35 g (0.51 mol) of sodium nitrite, 18 g (0.17 mol) of sodium carbonate, 140 ml of water and 2 g (0.007 mol) of tetrabutyl-phosphonium chloride is heated, in an autoclave, to 140° C. for 5 hours, whilst stirring and under the autogenous pressure. After cooling, the solid product is filtered off and washed with concentrated hydrochloric acid until no further evolution of gas can be discerned. The residue on the filter is then stirred with 30 ml of alcohol and the mixture is filtered. The residue is recrystallised from alcohol. 13.5 g (40% of theory) of 2,2'-dinitrodiphenyl ether (melting point: 112°-114° C.) are obtained.

EXAMPLE 4

A mixture consisting of 60 g (0.87 mol) of sodium nitrite, 53 g (0.5 mol) of sodium carbonate, 7 g (0.023 mol) of tetrabutyl-phosphonium chloride, 200 ml of water and 96 g (0.5 mol) of 3,4-dichloro-nitrobenzene is heated, in an autoclave, to 140° C. for 7 hours, under the autogenous pressure. After cooling, the precipitate is filtered off and washed, first with concentrated hydrochloric acid, then with a little water and finally with a little alcohol. The product which remains is recrystallised from alcohol. 40 g (48% of theory) of 2,2'-dichloro-4,4'-dinitro-diphenyl ether (melting point: 148°-149° C.) are obtained.

EXAMPLE 5

A mixture consisting of 40 g (0.58 mol) of NaNO$_2$, 20 g (0.19 mol) of sodium carbonate, 40 ml of water, 20 ml (0.03 mol) of a 50% strength solution of benzyldodecyl-dimethyl-ammonium chloride and 31 g (0.2 mol) of 2-chloro-6-fluorobenzonitrile is heated to the reflux temperature (110° C.) for 4 hours, whilst stirring. The (upper) organic phase is then separated off and cooled. The solid mass which is obtained is then recrystallised from isopropanol. 23.6 g (82% of theory) of 3,3'-dichloro-2,2'-dicyano-diphenyl ether (melting point: 194°-195° C.) are obtained.

2-Chloro-6-fluoro-benzonitrile, which was used as the starting compound, was obtained as follows:

A solution of 120 g (2 mols) of potassium fluoride in 100 ml of water was treated first with 30 ml of a 50% strength aqueous solution of benzyldodecyl-ammonium chloride and then with a solution of 186 g (1 mol) of 2-nitro-6-chloro-benzonitrile in 250 ml of toluene. The reaction mixture was heated to 105° C. for 8 hours.

After cooling, the organic phase was separated off and the aqueous phase was extracted with chloroform. The organic phase and the chloroform extracts were combined and washed and then freed from the organic solvent by distillation. On distillation of the residue, 35 g of 2-chloro-6-fluoro-benzonitrile (boiling point: 105°-108° C./15 mm Hg) were obtained.

EXAMPLE 6

A mixture of 69 g (1.0 mol) of sodium nitrite, 53 g (0.5 mol) of sodium carbonate, 5 g (0.01 mol) of hexadecyl-tributyl-phosphonium bromide, 220 ml of water and 78.5 g (0.5 mol) of 4-chloro-nitrobenzene is heated to 140° C. for 7 hours. After cooling, the solid product is filtered off and washed, first with a little dilute hydrochloric acid and then with a little alcohol. After drying, 61 g (91.5% of theory) of 4,4'-dinitrodiphenyl ether (melting point: 139°-140° C.) are obtained.

EXAMPLE 7

A mixture consisting of 8 g (0.115 mol) of sodium nitrite, 5 g (0.05 mol) of sodium carbonate, 1 g (0.0029 mol) of cyclohexyloctyldimethyl-ammonium chloride, 13 ml of water and 12 g (0.049 mol) of 4-chlorophenyl-trifluoromethylsulphone is heated to the reflux temperature for 3 hours. After cooling, the reaction mixture is extracted with 50 ml of methylene chloride. The organic phase is separated off, dried over sodium sulphate and freed from the solvent by distillation. The residue is recrystallised from n-hexane 8 g (75% of theory) of 4,4'-di-(trifluoromethylsulphonyl)-diphenyl ether (melting point: 102°-104° C.) are obtained.

What is claimed is:

1. In a process for the preparation of a diphenyl ether substituted in the 4,4'-position and/or the 2,2'-position relative to the ether oxygen atom by reaction of a reactive benzene compound substituted in the 1- and in the 2- or 4-position, said reactive benzene compound having the formula

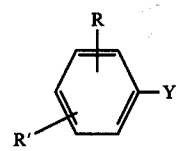

in which Y denotes a halogen atom or the nitro group, R denotes an NO$_2$, CN or R"SO$_2$ group which is in the ortho-position or para-position relative to Y, and R' denotes hydrogen fluorine, chlorine, a C$_1$–C$_4$-alkyl, C$_1$–C$_4$-alkoxy or C$_1$–C$_4$-alkylmercapto radical, which is optionally substituted by halogen, or the N(R")$_2$ radical in which R" represents alkyl or aryl which is optionally substituted by halogen, with an alkali or alkaline earth metal nitrite at 100°-220° C., the improvement which comprises carrying out the reaction in the presence of a quaternary onium salt in water, said quaternary onium salt having the formula

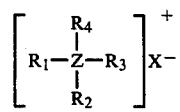

in which Z represents nitrogen or phosphorous, R$_1$, R$_2$, R$_3$ and R$_4$ represent C$_{1-18}$ alkyl radicals, aralkyl radicals in which the aryl portion is a benzyl radical which is optionally substituted by $C_{1-4}$ alkyl radicals, a methoxy group or halogen, a phenyl radical which is optionally substituted by $C_1$–$C_4$ alkyl, $C_1$–$C_2$ alkoxy or by halogen or a cycloalkyl radical selected from the group consisting of cyclopentyl and cyclohexyl which cycloalkyl radical can be optionally substituted by a $C_1$–$C_4$ alkyl radical, or two adjacent radicals amongst $R_1$, $R_2$, $R_3$ and $R_4$ together with the central atom Z and optionally further hetero-atoms, form a heterocyclic structure containing oxygen, sulfur or nitrogen in the ring, said heterocyclic structure being a 5- or 6-membered ring and $X^-$ represents a halide, cyanide or hydroxy ion.

2. A process according to claim 1, wherein:
A. The quaternary onium salt is selected from the group consisting of tetraethyl-ammonium chloride, tetrabutyl-ammonium bromide, tetrabutyl-ammonium iodide, triethyl-benzyl-ammonium chloride, methylbutyl-piperidinium iodide, tetraethyl-ammonium bromide, tetrabutyl-ammonium chloride, benzyl-methylpiperidinium iodide, tetraethyl-ammonium cyanide, benzyltrimethyl-ammonium hydroxide, benzyltrimethyl-ammonium cyanide, triphenylbenzyl-phosphonium bromide, benzyldodecyldimethyl-ammonium chloride, cyclohexyloctyldimethyl-ammonium chloride and tetrabutyl-phosphonium chloride;
B. The quaternary onium salt is present in the reaction mixture in an amount of 0.1 to 10% by weight; and
C. The process is conducted at a temperature of 100°–150° C.

3. A process according to claim 2, wherein the process is carried out in an autoclave.

* * * * *